United States Patent [19]

Aizawa et al.

[11] Patent Number: 5,569,860
[45] Date of Patent: Oct. 29, 1996

[54] METHOD OF ANALYTICALLY DETERMINING OPTIMUM CONDITIONS FOR POWDER FORGING

[75] Inventors: Tatsuhiko Aizawa, Tokyo; Takeshi Inao, Shiga, both of Japan

[73] Assignee: Murata Manufacturing Co., Ltd., Japan

[21] Appl. No.: 422,126

[22] Filed: Apr. 13, 1995

[30]    Foreign Application Priority Data

May 10, 1994 [JP] Japan .................................. 6-096553

[51] Int. Cl.$^6$ .................................................. G01N 1/00
[52] U.S. Cl. ............................................ 73/863; 73/866
[58] Field of Search ........................... 73/790, 863, 866

[56]             References Cited

U.S. PATENT DOCUMENTS 4,567,774  2/1986  Manahan et al. ....................... 73/862
4,617,817  10/1986  Gregel et al. ........................... 72/364
4,762,679  8/1988  Gegel et al. ............................ 73/863
5,402,366  3/1995  Kihara et al. ........................... 73/826

*Primary Examiner*—Richard Chilcot
*Assistant Examiner*—Max H. Noori
*Attorney, Agent, or Firm*—Majestic, Parsons, Siebert & Hsue

[57]             ABSTRACT

Optimum conditions for extrusion forging by using a powder material are determined by making a cylindrical billet out of the powder material, subjecting it to a deformation stress between plates to measure its strain as well as the time-rate of change in the strain, thereby determining parameters in the stress-strain formula, and carrying out a simulation analysis by an arbitrary Lagrangian-Eulerian method with an equation of motion obtained by the principle of virtual power. In considering the virtual power, bulk work is also taken into consideration. By such simulation analysis, data such as pressure distribution, speed distribution and density distribution are obtained. Optimum conditions are obtained by analyzing these data.

20 Claims, 3 Drawing Sheets

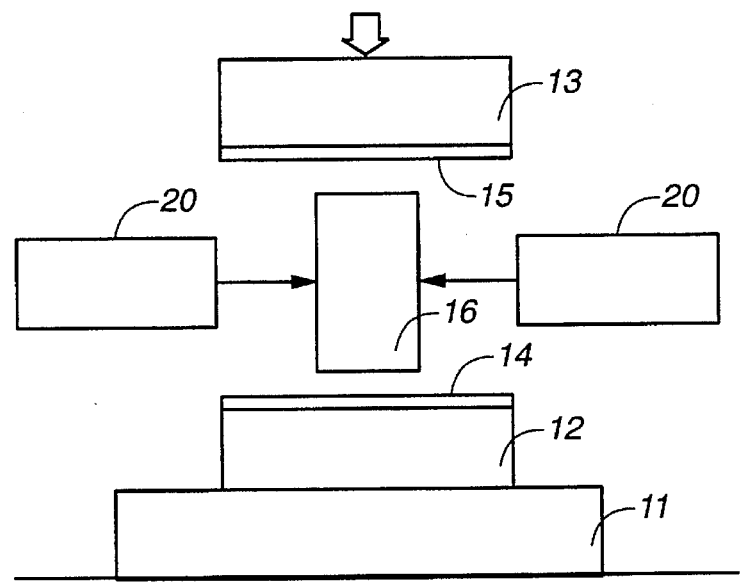
FIG._1
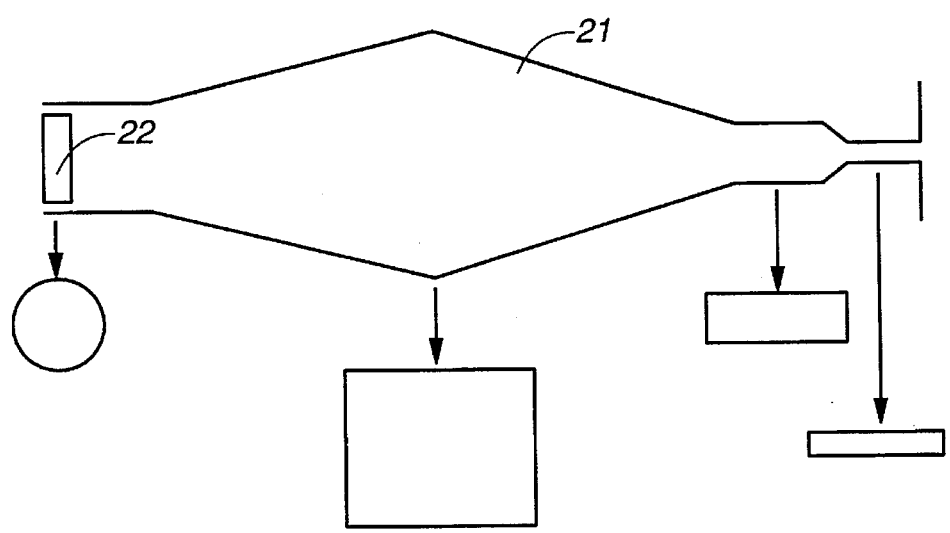
FIG._2

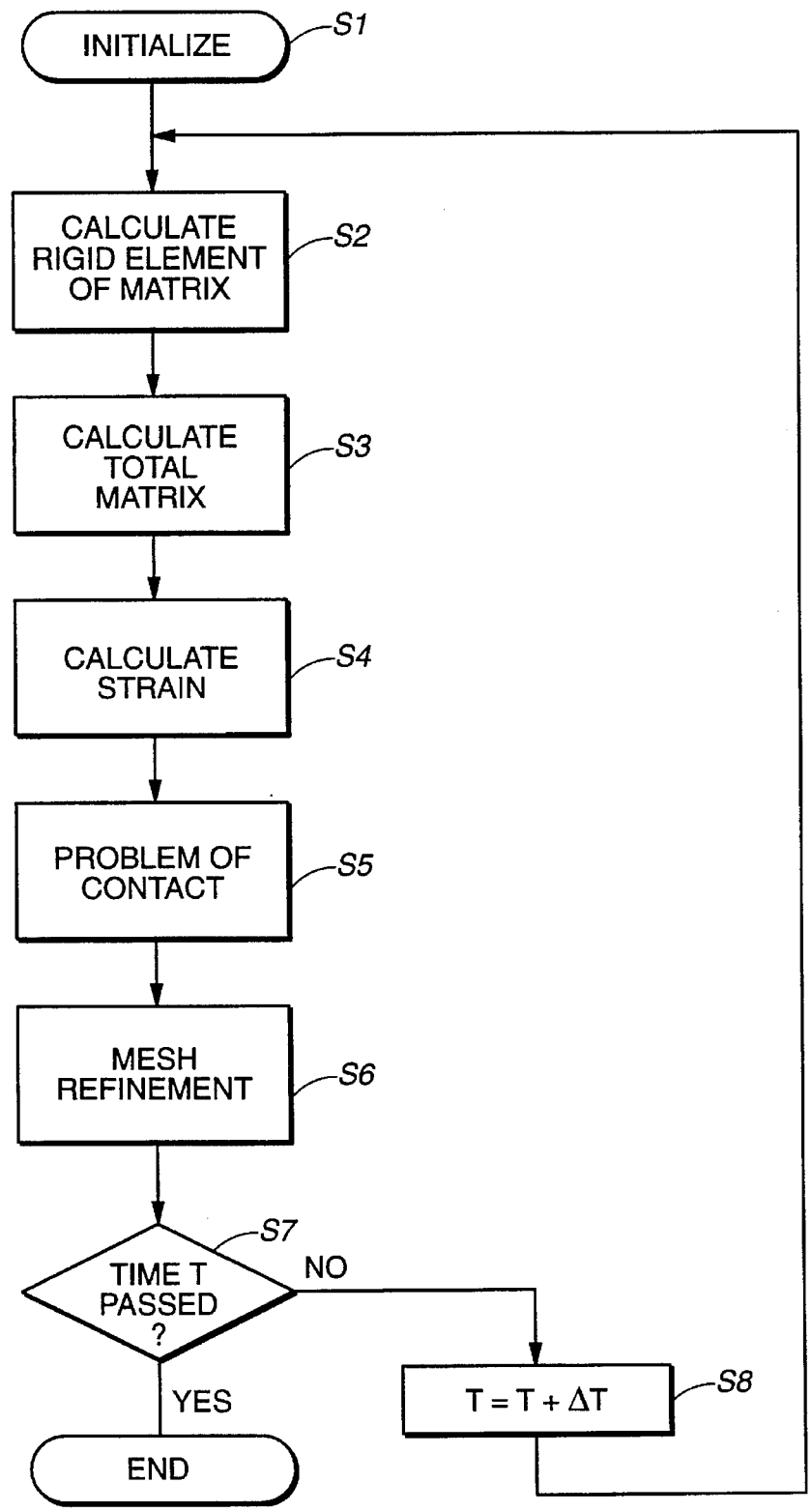
FIG._3

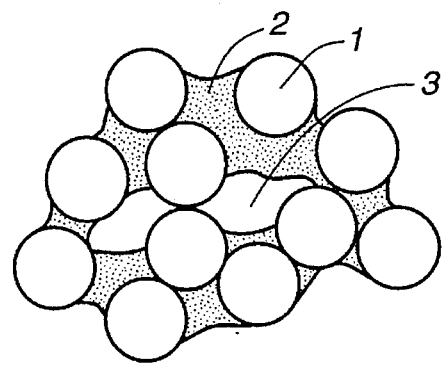
FIG._4
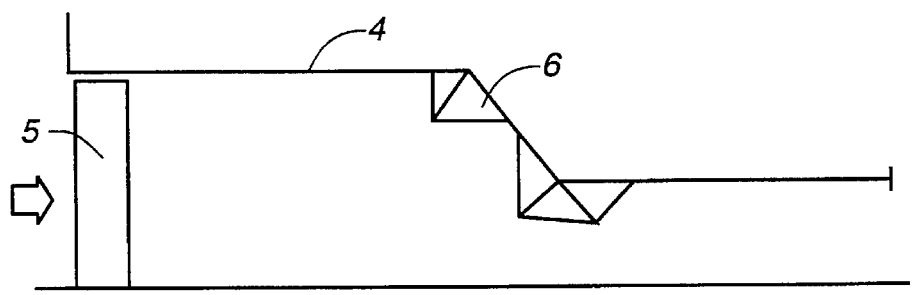
FIG._5 (PRIOR ART)
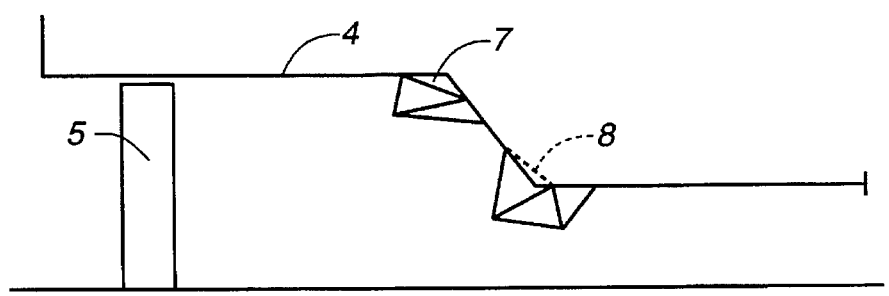
FIG._6 (PRIOR ART)

5,569,860

METHOD OF ANALYTICALLY DETERMINING OPTIMUM CONDITIONS FOR POWDER FORGING

BACKGROUND OF THE INVENTION

This invention relates to analytical methods of optimizing conditions for powder forging and, more particularly, to methods of optimizing the design of a die, operational conditions for the forging process such as pressure and flow rate and/or conditions on the materials such as the mixing ratio of the liquid, binder and powder material, as well as the particle size distribution.

When an extrusion forging process using a metallic powder material is analyzed by a finite element method, only shearing work (defined as the product of shearing strain and distance moved) is required to be considered, and there is no need to consider the bulk work (defined as the product of the bulk pressure due to a volume change and distance) because metallic powder materials consist of perfect arrays of electrons and their atomic configurations do not collapse even if pressure is applied. However, there have hardly been any attempts to carry out a three-dimensional finite element analysis for the forging process for a bulk metal.

In the case of powders of ceramic materials, by contrast as schematically shown in FIG. 4, particles 1 touch one another directly in some parts, while they touch one another through a liquid 2 or a gas phase 3 in some other parts. Although its overall shape will change when an external force is applied, there will be no such overall deformation in the absence of any external force. In a finite element analysis of powder forging such as forging by extrusion of such a material, therefore, the ratio of bulk work to internal work (defines as the sum of shearing work and bulk work) is not negligible. In other words, a plastic flow cannot be analyzed with high accuracy by computer simulation with a software program designed for finite element analysis for the case of a metallic material.

FIGS. 5 and 6, in which only the upper half of a die 4 is shown cross-sectionally, illustrate the finite element method of analysis by conventional Lagrangian description. If the interior of the die 4 is filled with a material in the condition illustrated in FIG. 4 (only five elements 6 for a finite element method of analysis being shown in FIG. 5 for convenience), and if this material is pushed from one side by a pressure-applying member 5, there may arise gaps 7 between the undeformable inner wall of the die 4 and the elements 6 and/or penetrations 8 of the die wall by an element 6 used in the finite element method of analysis as shown in FIG. 6. Consequently, the conservation of volume may fail to hold according to a conventional method of analysis. In other words, errors are introduced, and accurate calculations are impossible. Thus, three-dimensional dies could not be analyzed by a prior art method, and there has not been developed a system incorporating the arbitrary Lagrangian-Eulerian (ALE) method which is adapted to situations where contacts may exist between a powder material and a non-deformable tool.

SUMMARY OF THE INVENTION

It is therefore an object of this invention to provide analytical methods of finding optimum conditions for powder forging such as relating to the design of the die, operational conditions for the forging process such as pressure and flow rate and/or conditions related to the materials such as the mixing ratio of the liquid, binder and powder material, as well as the particle size distribution.

According to a method embodying this invention, with which the above and other objects can be accomplished, parameters for formulas for characteristics of materials (say, for the deformation stress on the powder material as a function of strain and its time-derivative) are determined by making measurements, and such formulas are used in an equation of motion obtained by the principle of virtual power, including bulk work as well as shearing work, for carrying out simulation by arbitrary Lagrangian-Eulerian method. Data such as pressure distribution, velocity distribution and density distribution are outputted, and these outputted data are analyzed. Input data are modified according to the analyzed output date to repeat the process. Thus, the design of the die, conditions of the forging process and the conditions on the material to be used can be optimized. Alternatively, the parameters of the aforementioned formulas may be determined by individually evaluating characteristics of powder materials and liquids to be added thereto and by considering their mixing ratio.

BRIEF DESCRIPTION OF THE DRAWINGS

The accompanying drawings, which are incorporated in and form a part of this specification, illustrate an embodiment of the invention and, together with the description, serve to explain the principles of the invention. In the drawings:

FIG. 1 is a schematic diagram for showing an apparatus for measuring strain and time-rate of change in strain of a billet according to this invention;

FIG. 2 is a schematic sectional view of a die for forming a sheet by an extrusion forging process;

FIG. 3 is a flow chart of an analytical process according to a method embodying this invention;

FIG. 4 is a schematic diagram showing the structure of a ceramic powder; and

FIGS. 5 and 6 are schematic sectional views of a portion of the interior of a die, showing the prior art finite element method of analysis, as well as problems with the method.

DETAILED DESCRIPTION OF THE INVENTION

As shown in FIG. 1, a sample billet 16, prepared at a specified mixing ratio in a cylindrical form, is placed between an lower plate 12 and an upper plate 13 of a device according to this invention. The lower plate 12 is set upon a load cell 20 serving as a load-detecting means. Teflon (polytetrafluoroethylene) sheets 14 and 15 with a relatively small coefficient of friction are provided respectively on the upper surface of the lower plate 12 and the lower surface of the upper plate 13 for preventing the billet 16 from becoming deformed into a barrel-like shape when a pressure is applied thereon from above by the upper plate 13.

As the upper plate 13 is lowered towards the lower plate 12 at a constant speed to compress the billet 16, the reaction force P from the billet 16 is measured by the load cell 11. As the height of the billet 16 is reduced thus at this constant rate, the diameter d of the cylindrical billet 16, which increases simultaneously, is measured by laser-assisted instruments 20 for measuring lengths. The stress $\sigma$ operating in the axial direction for causing the deformation is expressed as follows:

$$\sigma = P/(\Pi d^2/4) = f(\epsilon, \dot\epsilon) \tag{1}$$

where $\epsilon$ is the strain, or the fractional change in the diameter d, and $\dot\epsilon$ is the time-rate of change in $\epsilon$.

Let us assume that the function $f(\epsilon, \dot\epsilon)$ is in the form given below:

$$\sigma = k \cdot \epsilon^n \cdot \dot\epsilon^m \tag{2}$$

where k, m and n are constants, of which the values can be experimentally determined by making measurements on a plurality (say, three or four) of billets. Once the values of these constants are determined, simulation calculations become possible.

It is to be noted that Formula (2) does not take the existence of cavities into account. The void ratio $f_v$, or the apparent density, is given by:

$$f_v = 1/\{a(1-\rho)^h\}, \tag{3}$$

where $\rho$ is the density ratio, or the ratio between the real density and the apparent density of the billet, and a and h are constants dependent upon the material of the billet.

If the aforementioned internal work is balanced with the external work with respect to any element (with volume V and surfaces $S\sigma$) according to the principle of virtual power, one obtains an equation of motion:

$$\int_V S_{ij} \delta \dot\epsilon_{ij} dV + \int_V p \delta \dot\epsilon_{ij} dV = \int_{S\sigma} T_i \delta V_i dS_i \tag{4}$$

where the first term on the left-hand side of the equation represents the shearing work, and the second term on the left-hand side represents the bulk work. On the right-hand side, $T_i$ represents the external force and $\delta v_i$ represents the increment in speed. Thus, the term on the right-hand side represents the external work which balances the inner work on the left-hand side of the equation. The shearing strain, $S_{ij}$, is obtained from the Levy-Mises stress-strain relationship, $\delta \dot\epsilon_{ij}$ represents the increment in $\dot\epsilon_{ij}$.

The billet is forged into the form of a sheet as shown in FIG. 2 by means of a die 21 having a circular cross-section near its inlet and a quadrangular cross-section at the center. From the center section to its outlet, the cross-sectional shape changes gradually to a thinner rectangle, reducing its thickness. Pushed at a constant pressure p by a plunger 22 provided at the inlet, a powder material is formed into a shape with a quadrangular cross-section at the center section and emerges as a sheet at the outlet.

Steady-state flow analyses are carried out by an arbitrary Lagrangian-Eulerian method with the equation of motion as given by Formula (4) and under the condition that the pressure p at the inlet and the extrusion speed v at which the sheet is taken out at the output are both constant. Unsteady-state flow analyses are also carried out likewise by keeping the pressure constant at the inlet but by treating the speed v at the outlet as an unknown. Pressure distribution inside the forged sheet, velocity distribution and density distribution are outputted from such simulation analyses by using different input parameters such as relating to the shape of the die and characteristics of the powder material. By comparing these input and output data, it is possible to optimize not only the shape of the die and the powder material but also conditions of the forging operation. As a result, the shape and the accuracy in dimensions of the forged object can be improved and its density distribution can be made uniform. This means that forged objects of high quality, as designed, can be obtained at a reduced cost. FIG. 3 shows the flow of calculations according to a finite element analysis according to this invention. After a standard initialization step (S1), a rigid matrix is formed for each element (S2), and a total matrix is obtained therefrom (S3). Equations of motion are thus obtained for all elements from Formula (4), and strain values are obtained by solving these equations of motion (S4). Next, the problem of material-tool contact is addressed to by checking whether or not the nodes after the deformation are on the material-tool contact surface, or the inner surface of the die 21 (S5). Whenever a new node comes into contact, the elements associated with such a node are re-generated for the next cycle of the calculation (S6). These steps are repeated after a predetermined incremental time interval $\Delta T$ (S8) until a predetermined total time of operation T has elapsed (S7).

Although this invention has been described above with reference to only one example, this example is intended to be illustrative, not as limiting. Many modifications and variations are possible within the scope of this invention. For example, although a forged sample body was subjected to pressure along an axis to find material constants according to the method described above, this makes it necessary to make clay-like samples by varying the mixing ratio between powder material and water to measure material characteristics. Thus, material characteristics can be measured only with materials with shape-preserving characteristic when forged to form a billet. In other words, the scope of materials for which the method can be used is too narrow.

For this reason, according to a preferred embodiment of this invention, not only characteristics of powder materials (such as particle shape, particle density and particle size distribution) and those of the liquid to be added (such as viscosity) but also other basic characteristics of the material such as the mixing ratio of the liquid with respect to the powder material are preliminarily inputted. Thereafter, characteristics of a given material are evaluated by computer simulation by varying the mixing ratio, particle size distribution and other conditions. After the constants in Formulas (2) and (3) are determined, simulation analyses as described above can be carried out by using such constants.

In summary, deformation (or strain) of a billet and its speed (or time-rate thereof) are measured, for example, to derive formulas for material characteristics, and an equation of motion is obtained by incorporating such formulas and by the principle of virtual power. The equation is solved for each element used in an analysis by the finite element method. Pressure distribution, speed distribution and density distribution can be outputted as a result of such a simulation process. It is possible, by collecting these outputted data and repeating the calculations by varying input conditions, to optimize the shape of the die, conditions of the forging process and the material used for the forging process.

What is claimed is:

1. A method of determining optimum conditions for extrusion forging by using a ceramic powder material, said method comprising the steps of:

deriving a formula for a material characteristic of said powder material by measuring strain and time-rate of change in strain of a billet formed with said powder material;

obtaining an equation of motion by the principle of virtual power by incorporating said derived formula and including bulk power in said virtual power;

solving said equation of motion by a finite element method to carry out simulation calculation of said extrusion forging;

outputting data obtained by said simulation calculation; and repeating the steps above by comparing said outputted data and thereby determining optimum conditions for said extrusion forging.

2. The method of claim 1 wherein said outputted data include one or more selected from the group consisting of pressure distribution, speed distribution and density distribution in a forged product obtained by said simulation calculation.

3. The method of claim 2 wherein said simulation calculation is carried out by the Arbitrary Lagrangian-Eulerian method.

4. The method of claim 1 wherein said formula is for deformation stress expressed as a function of strain and time rate of change of strain.

5. The method of claim 1 wherein said formulas include a formula for void ratio.

6. A method of determining optimum conditions for extrusion forging by using powder material, said method comprising the steps of:

deriving a stress formula for deformation stress of said powder material expressed as a function of strain and time rate of change of strain by measuring strain and time-rate of change in strain of a billet formed with said powder material;

determining a void ratio formula for void ratio of said powder material;

obtaining an equation of motion by a principle of virtual power by incorporating said stress formula and said void ratio formula and including bulk power in said virtual power;

solving said equation of motion by a finite element method to carry out simulation calculation of said extrusion forging;

outputting data obtained by said simulation calculation; and repeating the stems above by comparing said outputted data and thereby determining optimum conditions for said extrusion forging.

7. A method of determining optimum conditions for extrusion forging by using a powder material, said method comprising the steps of:

deriving a formula for a material characteristic of said powder material by measuring strain and time-rate of change in strain of a billet formed with said powder material;

obtaining an equation of motion by a principle of virtual power by incorporating said derived formula and including bulk power in said virtual power;

solving said equation of motion by a finite element method to carry out simulation calculation of said extrusion forging;

outputting data obtained by said simulation calculation;

repeating the step above by comparing said outputted data and thereby determining optimum conditions for said extrusion forging.

8. The method of claim 1 wherein said optimum conditions to be determined relate to the shape of a die used in said extrusion forging.

9. The method of claim 1 wherein said optimum conditions to be determined relate to conditions for carrying out said extrusion forging.

10. The method of claim 1 wherein said optimum conditions to be determined relate to the choice of said powder material.

11. The method of claim 1 wherein said material characteristics to be determined include deformation stress, said method further comprising the step of determining said deformation by placing a billet made in a cylindrical form from said powder material between an upper plate and a lower plate, applying a pressure on said billet from said upper plate to cause a strain, and measuring strain of said billet and time-rate of change in said strain.

12. The method of claim 6 wherein said outputted data include one or more selected from the group consisting of pressure distribution, speed distribution and density distribution in a forged product obtained by said simulation calculation.

13. The method of claim 12 wherein said simulation calculation is carried out by the Arbitrary Lagrangian-Eulerian method.

14. The method of claim 6 wherein said optimum conditions to be determined relate to the shape of a die used in said extrusion forging.

15. The method of claim 6 wherein said optimum conditions to be determined relate to conditions for carrying out said extrusion forging.

16. The method of claim 6 wherein said optimum conditions to be determined relate to the choice of said powder material.

17. The method of claim 6 wherein said material characteristics to be determined include deformation stress, said method further comprising the step of determining said deformation by placing a billet made in a cylindrical form from said powder material between an upper plate and a lower plate, applying a pressure on said billet from said upper plate to cause a strain, and measuring strain of said billet and time-rate of change in said strain.

18. The method of claim 7 wherein said outputted data include one or more selected from the group consisting of pressure distribution, speed distribution and density distribution in a forged product obtained by said simulation calculation.

19. The method of claim 18 wherein said simulation calculation is carried out by the Arbitrary Lagrangian-Eulerian method.

20. The method of claim 7 wherein said optimum conditions to be determined relate to the shape of a die used in said extrusion forging.

* * * * *